United States Patent [19]
Crooks

[11] Patent Number: 5,652,965
[45] Date of Patent: Aug. 5, 1997

[54] NON-FOGGING GOGGLES

[76] Inventor: Dennis J. Crooks, 13983 Humo Dr., Poway, Calif. 92064

[21] Appl. No.: 353,805

[22] Filed: Dec. 12, 1994

Related U.S. Application Data

[63] Continuation-in-part of Ser. No. 71,668, Jun. 2, 1993, abandoned.

[51] Int. Cl.⁶ ........................................ A61F 9/02
[52] U.S. Cl. ........................................ 2/436
[58] Field of Search ........................ 2/436, 437, 452, 2/9, 171.3, 426

[56] References Cited

U.S. PATENT DOCUMENTS

| | | |
|---|---|---|
| 1,947,137 | 3/1934 | Fraser . |
| 4,286,340 | 9/1981 | Lathrop ........................... 2/452 |
| 4,731,885 | 3/1988 | Nava ........................... 2/436 X |
| 5,363,512 | 11/1994 | Grabos, Jr. et al. ............ 2/436 |

FOREIGN PATENT DOCUMENTS

| | | |
|---|---|---|
| 365848 | 2/1906 | France . |
| 0383159 | 12/1907 | France ........................... 2/436 |

*Primary Examiner*—Peter Nerbun
*Attorney, Agent, or Firm*—John R. Ross

[57] ABSTRACT

Non fogging goggles are disclosed. An air scoop is provided at the bottom side of the goggles providing an air port with a cross sectional area of at least 1 square inch open in the front side of said frame for permitting air to enter the goggles. When the user is facing into a head wind, which may be self created, air is forced into the-goggles so as to cause a positive air pressure. A valve located at the top side of the goggle controls the amount of air passing through the goggles. In a preferred embodiment the valve comprises a spacer with four square ports ½ inch on a side, two ports on each side. One port on each side is covered with very light foam screen. The other two ports are unrestricted. A slider contains two ½ inch square ports which can be aligned by the wearer over the screened ports in the spacer or the unrestricted ports. The screened ports are utilized while in motion or during driving snow storms. The unrestricted ports are utilized while motionless on windless days while standing in lift lines.

9 Claims, 12 Drawing Sheets

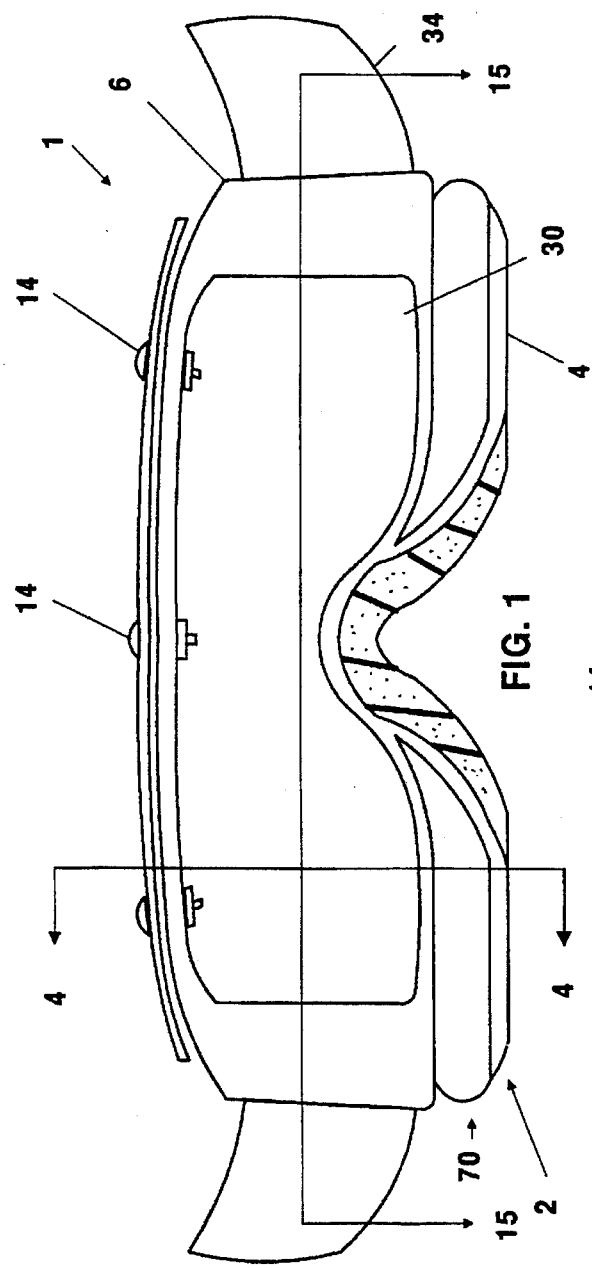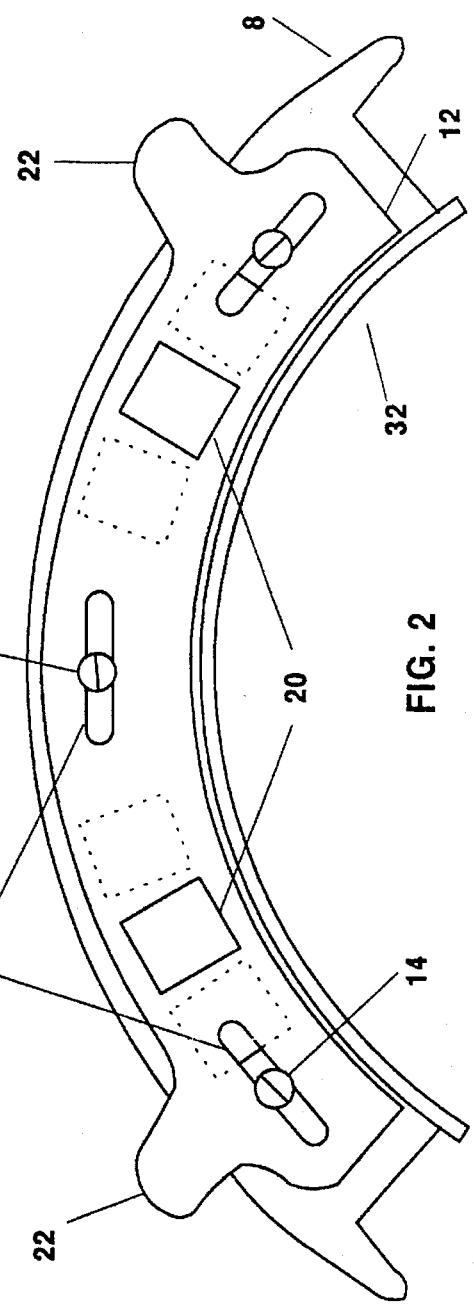

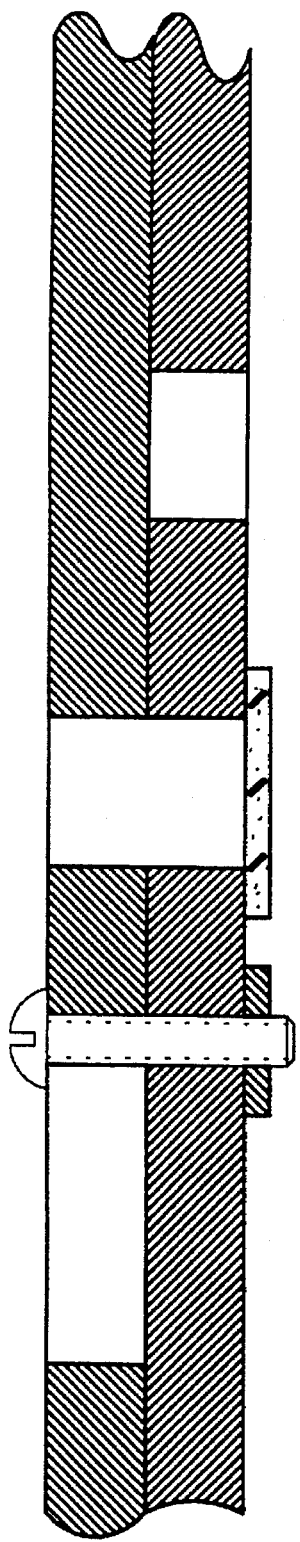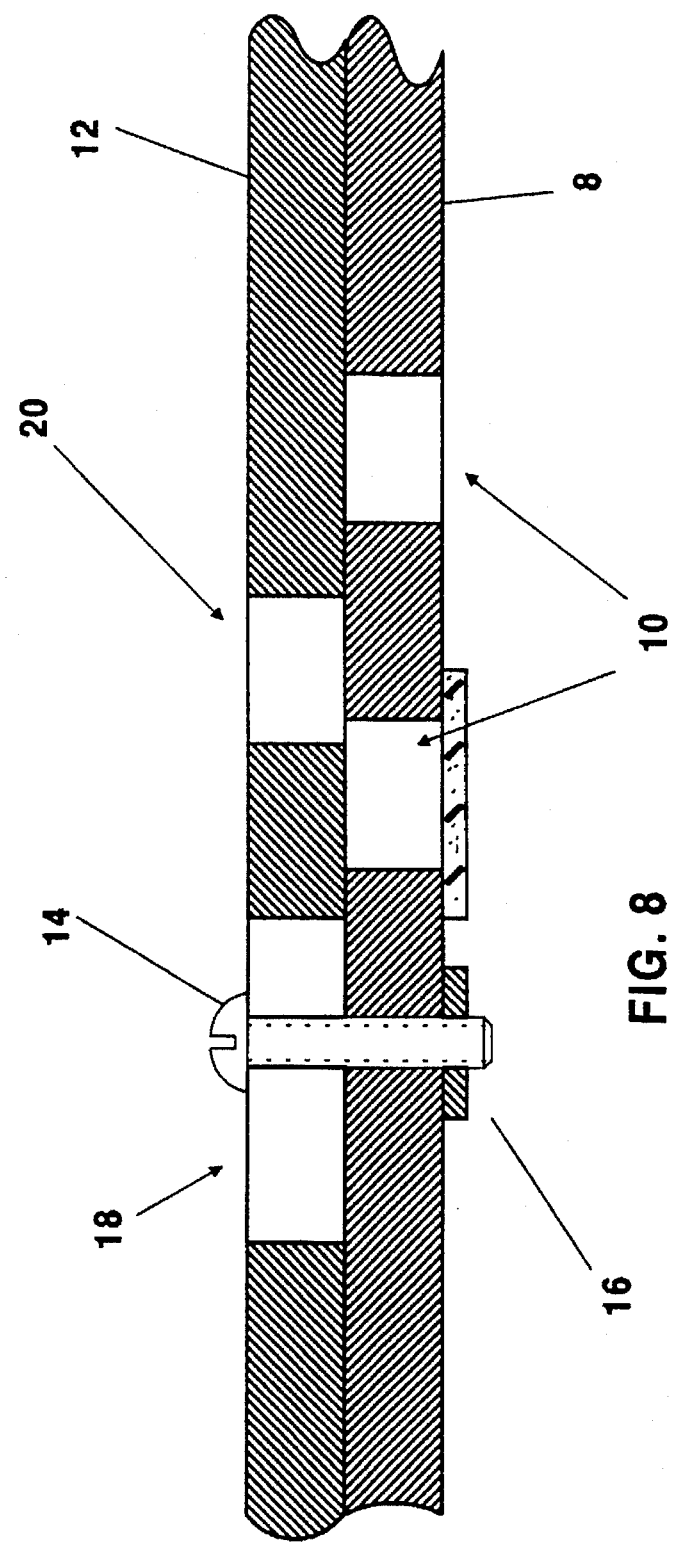

NON-FOGGING GOGGLES

This is a continuation in part application of Ser. No. 08/071,668, filed Jun. 2, 1993, now abandoned. The present invention relates to goggles and in particular to non-fogging goggles.

BACKGROUND OF THE INVENTION

Fogging of goggles by condensation of water vapor on goggle lenses has been a serious problem especially for snow skiers and motor cycle riders. Fogging of eye glasses inside goggles is also a problem for people who wear eye glasses. Attempts have been made to solve these problems. Dawson in U.S. Pat. No. 5,018,223 proposes a double lens with the inner lens coated with a metal coating, but there is no means for removal of warm moist air. (Metcalfe, U.S. Pat. No. 4,977,627, has proposed a ventilated protective goggle with snaps to cover the ventilation holes for use in case of a splash hazard. There is no contemplation by Metcalfe of forced air flow through the goggle.) McNeal in U.S. Pat. No. 4,707,863 proposes an anti-fog goggle with a foam frame and ventilation channels. Nesler, U.S. Pat. No. 4,435,852, proposes to use a venturi effect to suck air through his goggle to prevent fogging. Fraser, U.S. Pat. No. 1,947,137 proposes a venturi valve to suck moist air out of the goggle. Venturi valves are known in the prior art to produce vacuums in the air spaces in the goggles. Felix in French Patent No. 365,848 shows small scoops in the bottom of his patents, but he shows no means for controlling the air forced into the goggles.

SUMMARY OF THE INVENTION

The present invention provides non-fogging goggles. An air scoop is provided at the bottom side of the goggles providing an air port with a cross sectional area of at least 1 square inch open in the front side of said frame for permitting air to enter the goggles. When the user is facing into a head wind, which may be self created, air is forced into the goggles so as to cause a positive air pressure. A valve located at the top side of the goggle controls the amount of air passing through the goggles. In a preferred embodiment the valve comprises a spacer with four square ports ½ inch on a side, two ports on each side. One port on each side is covered with very light foam screen. The other two ports are unrestricted A slider contains two ½ inch square ports which can be aligned by the wearer over the screened ports in the spacer or the unrestricted ports. The screened ports are utilized while in motion or during driving snow storms. The unrestricted ports are utilized while motionless on windless days while standing in lift lines.

BRIEF DESCRIPTION OF THE DRAWINGS

FIG. 1 shows the front view of a preferred embodiment of the present invention.

FIG. 2 shows the top view of a preferred embodiment of the present invention with the ventilation control valve superimposed on the goggle body.

FIG. 7 shows a cross section of part of the valve of the preferred embodiment with the valve in the fully open position venting through very light foam screen.

FIG. 8 shows a cross section of part of the valve of the preferred embodiment with the valve in the partially open position venting through very light foam screen.

DETAILED DESCRIPTION OF PREFERRED EMBODIMENTS

Preferred embodiments of the present invention can be described by reference to the drawings.

First Preferred Embodiment

Figure 3:
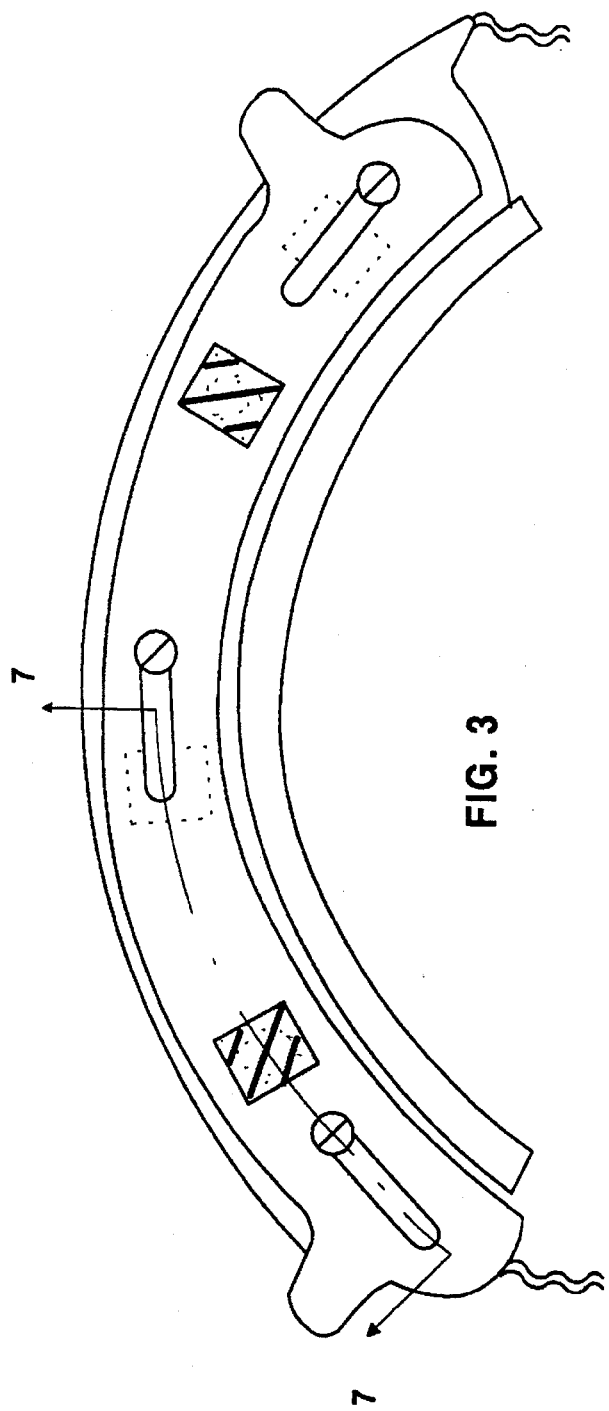
FIG. 3 shows the top view of a preferred embodiment of the present invention with the valve fully open in the "vent through foam" position.
Figure 10:
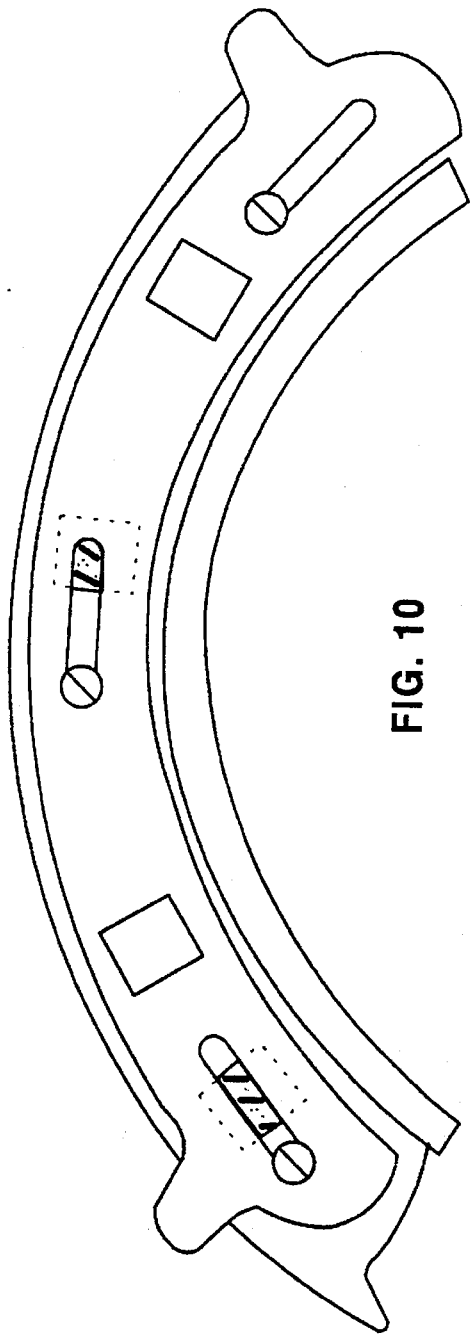
FIG. 10 shows a top view of a preferred embodiment of the present invention with the valve fully open in the "unrestricted vent" position.
Figure 11:
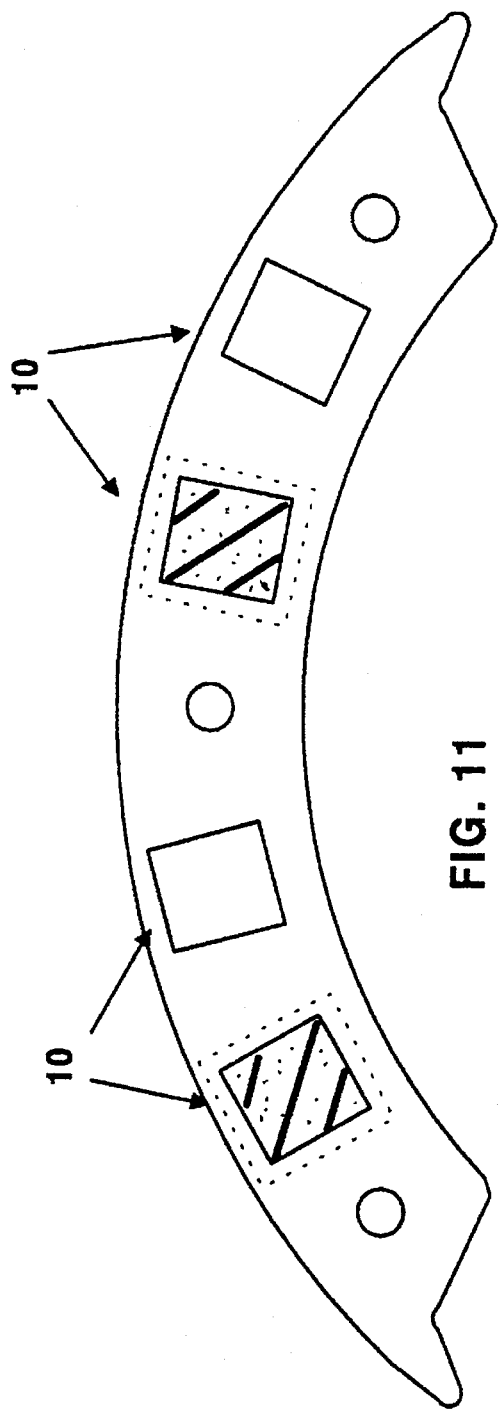
FIG. 11 shows a top view of a preferred embodiment of the present invention.
Figure 12:
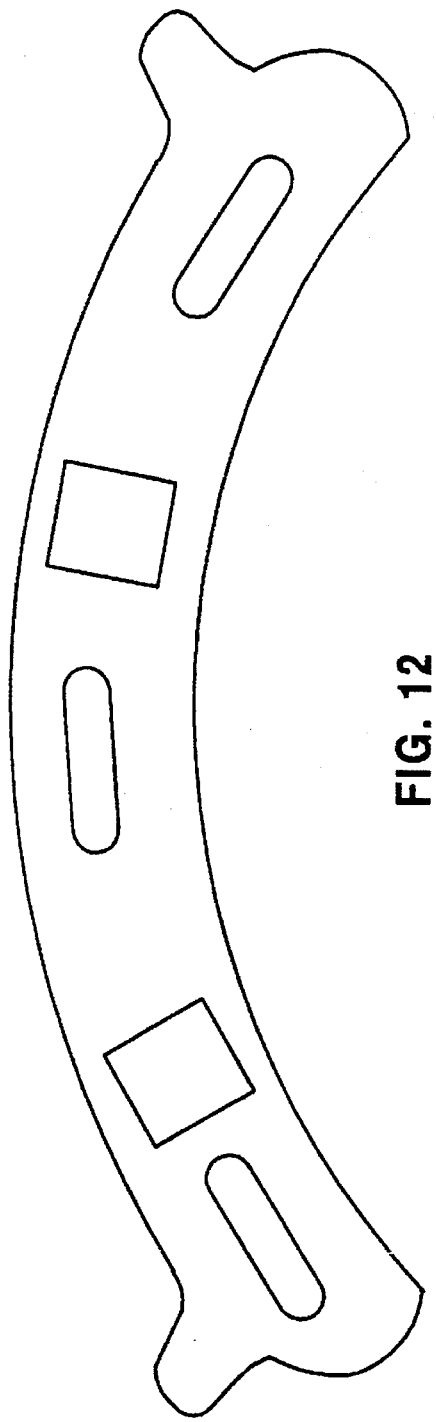
FIG. 12 shows a top view of a control valve.

As shown in FIG. 1 air scoops 2 at the bottom of both sides of goggles 1 are formed of strips 4 of soft pliable plastic glued to the frame 6 of goggle 1. Goggles 1 comprises top spacer 8 containing 4½ inch square ventilation holes 10 identified in FIG. 8 and FIG. 11. Two of the holes have a very light foam screen glued over the opening to prevent entry of snow or dust during windy conditions. The other two holes are open for unrestricted ventilation. Valve plate 12 is held slidably on top of top spacer 8 by three screws 14 which pass through slots 18, through top spacer 8 and are screwed into and through bar 16 which is a part of frame 6. Valve plate 12 also contains two square holes 20 (or ports) ½ inch on a side spacably matched to the holes in top spacer 8. Tabs 22 are used to slide valve plate 12 to the left and right to open and close ventilation passages formed of holes 10 and 20. The position to the wearers far left is full open and venting through foam as shown in FIG. 3, FIG. 7-7 and FIG. 4.

Figure 5:
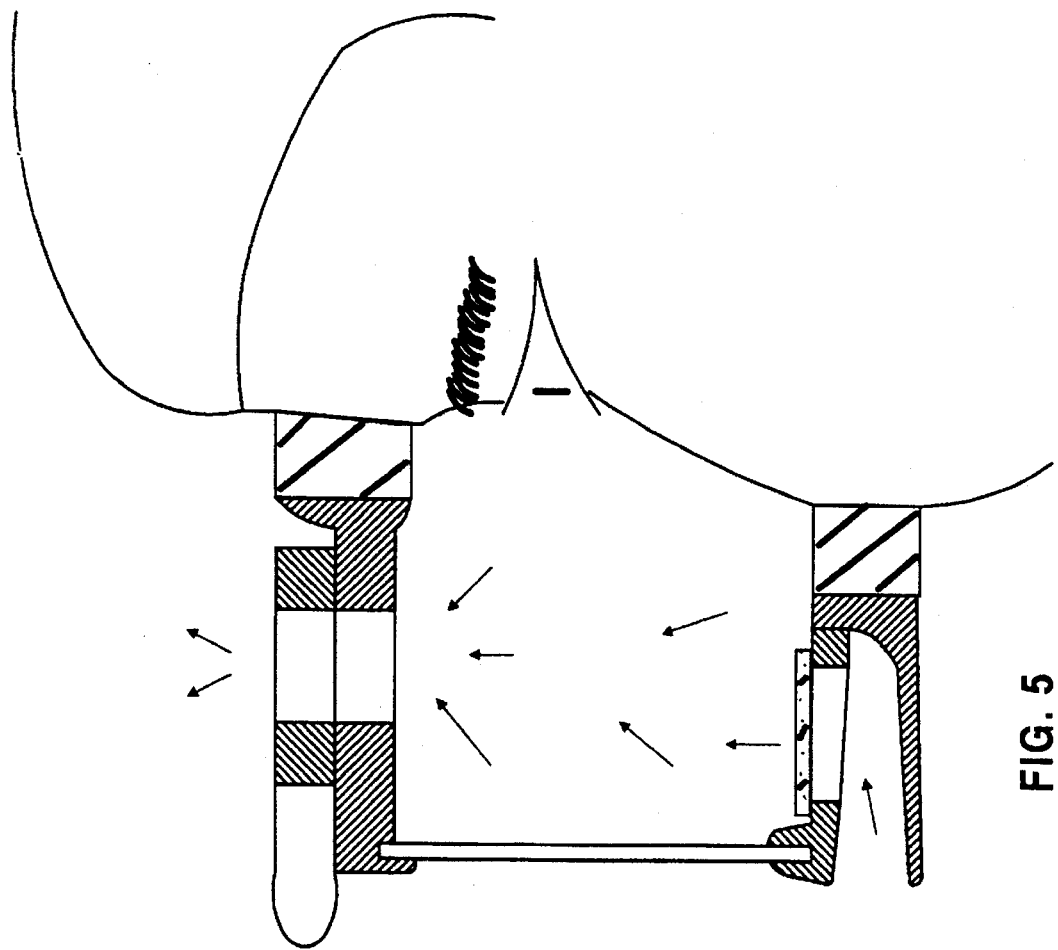
FIG. 5 shows a cross section of the embodiment on a wearer with the valve fully open through the unrestricted vent port.
Figure 4:
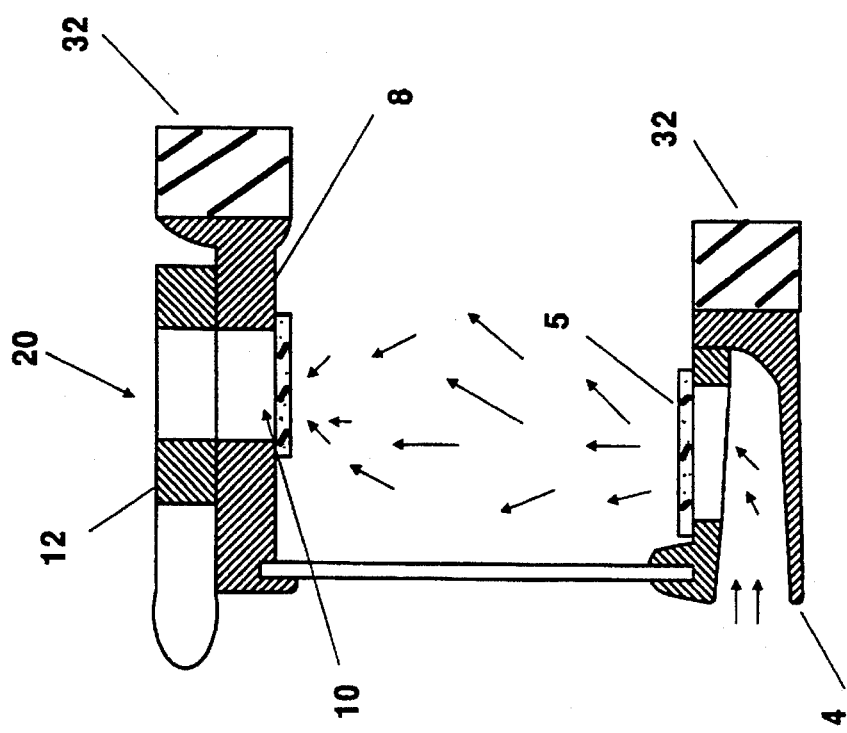
FIG. 4 shows a cross section of the "vent through foam" portion of the above preferred embodiment.
Figure 6:
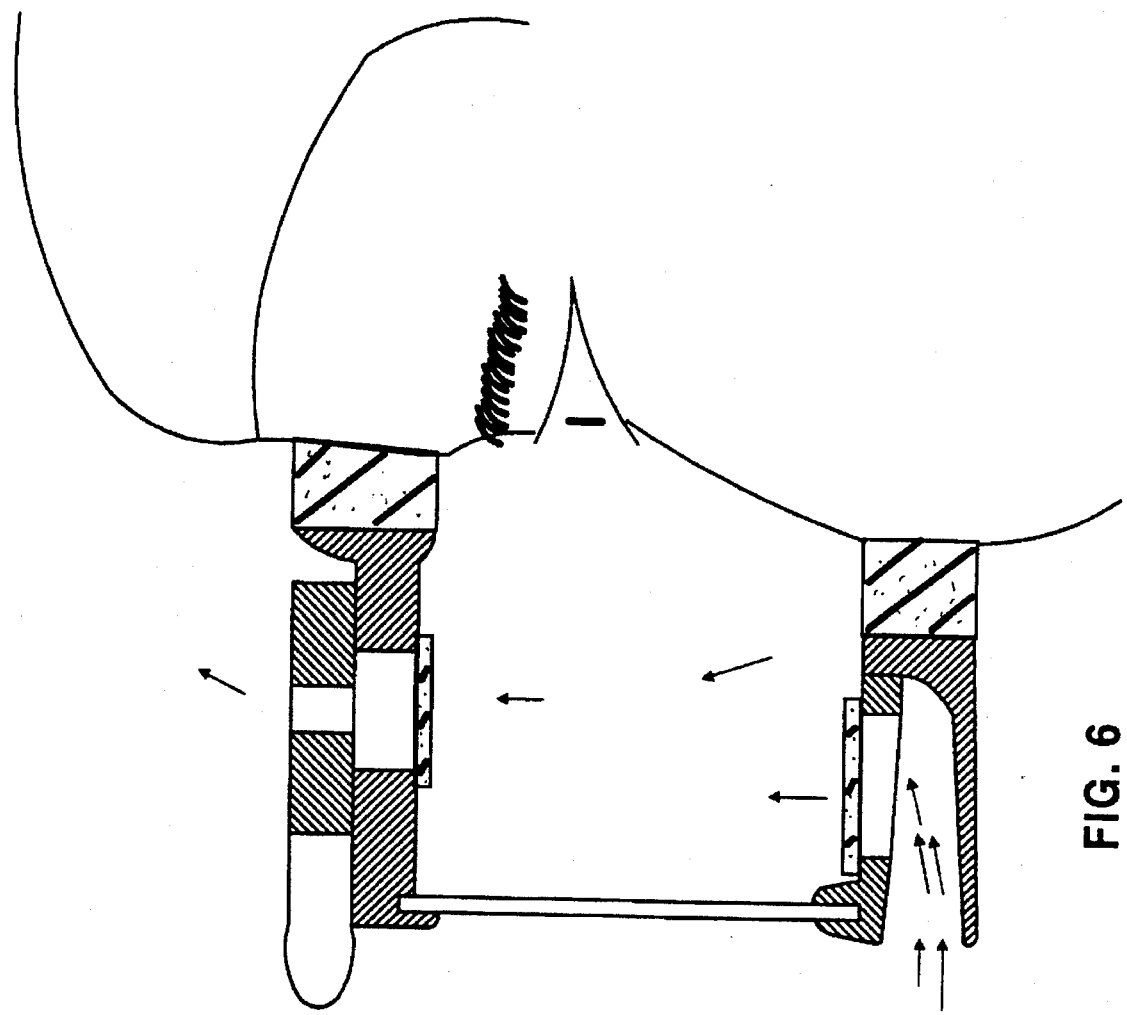
FIG. 6 shows a cross section of the embodiment on a wearer with the valve partially open venting through very light foam screen.

Air passes fairly freely through the goggle as shown in FIG. 4-4, especially when the wearer is facing into a wind which may be created by his forward motion as when he is skiing down hill or drives his motorcycle at a high rate of speed. Very light foam screen 5 at the bottom of goggle 1 permits air to pass into the goggle with a very slight pressure differential. If the volume of air entering the goggle is too great for the comfort of the wearer, he can partially close the ventilation valve by sliding valve plate 12 slightly to the wearer's right as shown in FIG. 8 and FIG. 6. This reduces the amount of air volume passing through the goggle as shown by comparing FIGS. 4-4 and 6. Sliding valve plate to the mid position as shown in FIG. 2 shuts the ventilation holes. Thus, a skier would partially close the ventilation valve before racing down hill and would open the valve to the unrestricted vent port as shown in FIG. 5 at the bottom of the hill. With the valve fully open convection through the space between the wearer's face and the lenses removes warm moist air to prevent condensation.

With the exception of the air scoops at the bottom and the valve at the top the goggle is a typical goggle comprising lens plate 30, sponge rubber seal-cushions 32, and head strap 34.

Second Preferred Embodiment

Figure 9:
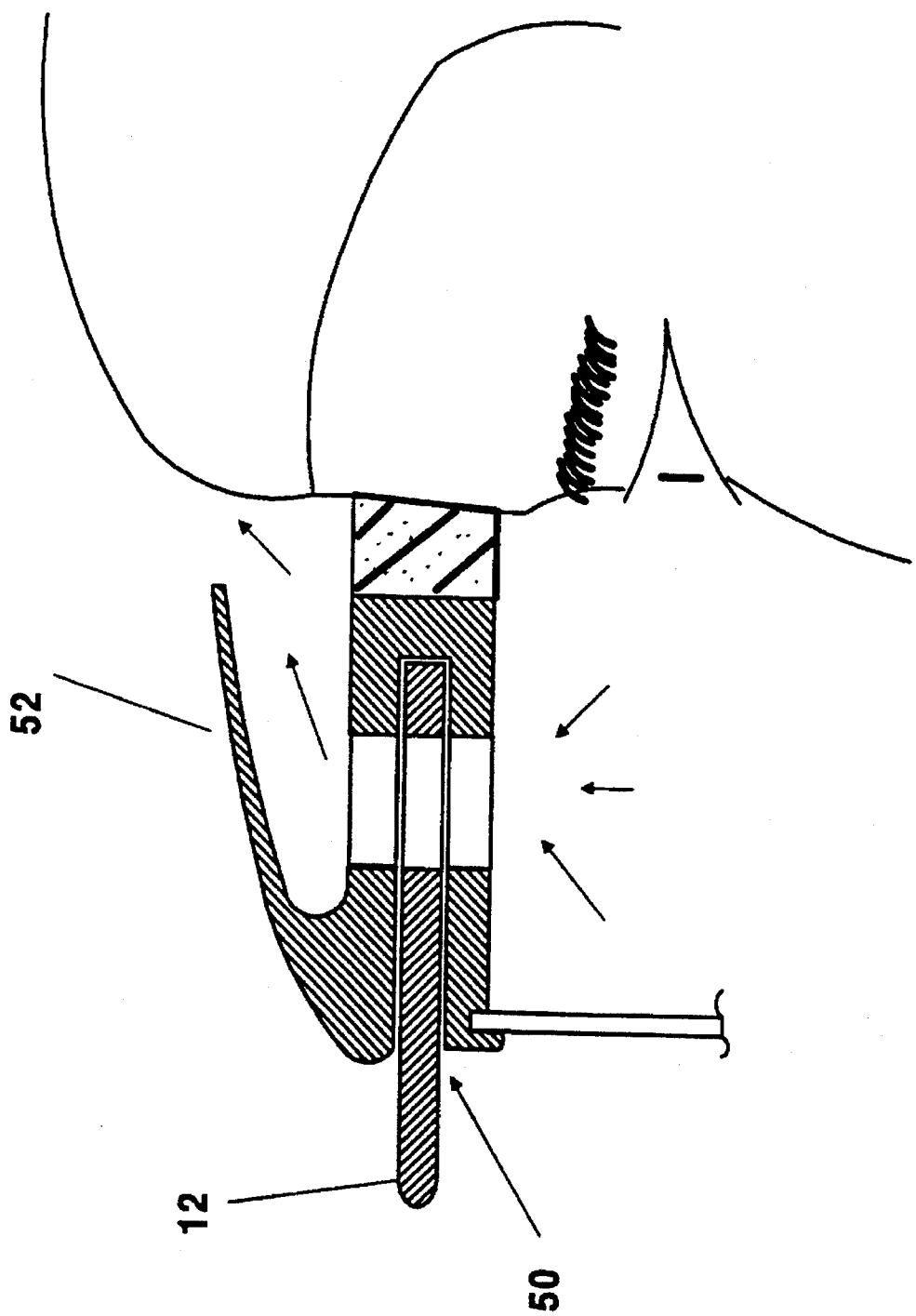
FIG. 9 is a cross section drawing showing a faring added to the goggle.

A portion of a second preferred embodiment is shown in FIG. 9. In this embodiment valve plate slides in pocket 50 which is molded as a part of the frame of the goggle. In this embodiment a faring 52 is provided which covers the valve and prevents snow and mud from covering the openings in the valve. Slide valve 12 is held in place as described above except that screws 14 (not shown) also pass through the bottom portion of faring 52.

Third Preferred Embodiment

Figure 13:
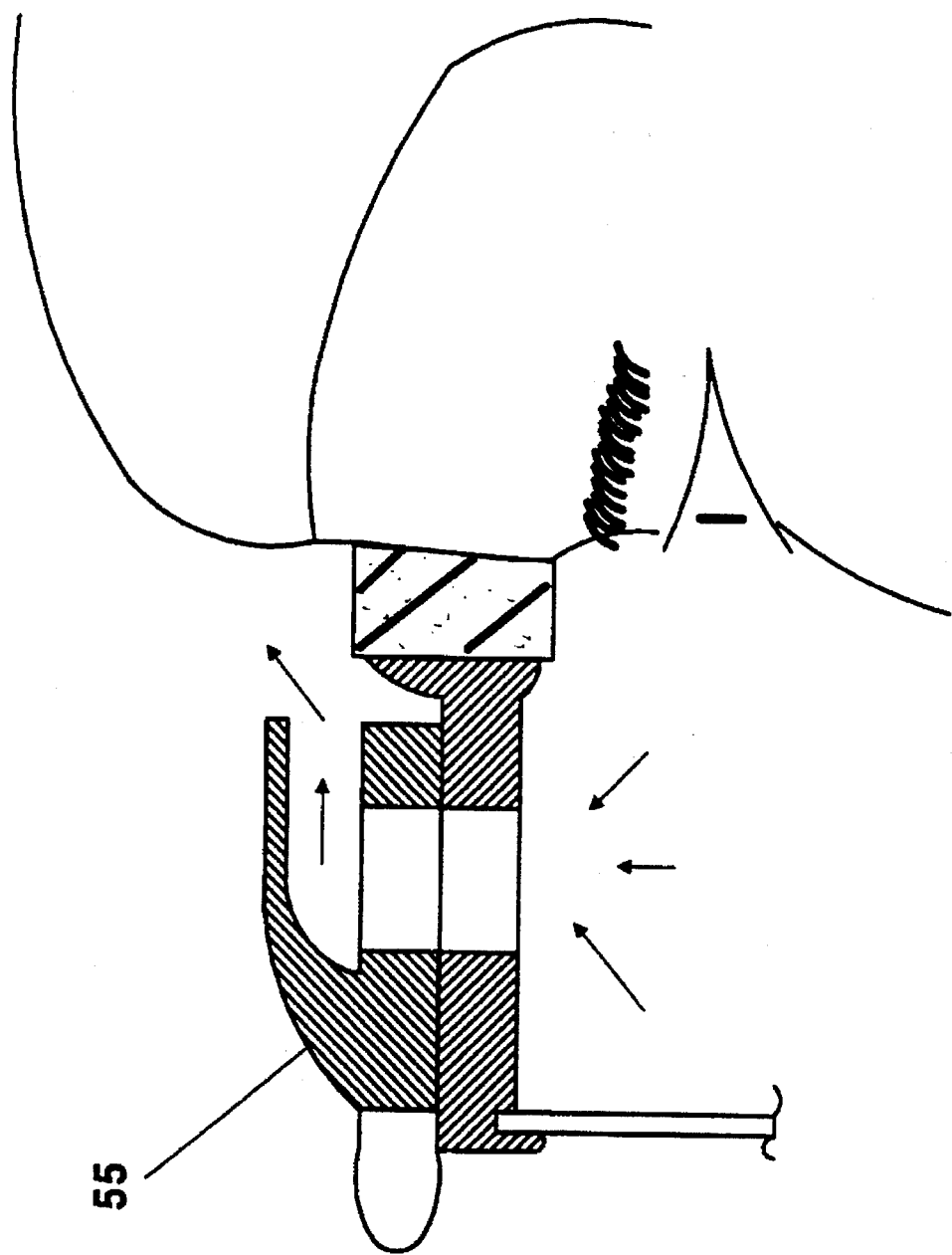
FIG. 13 is a cross section drawing showing a faring molded to the ventilation control valve.
Figure 14:
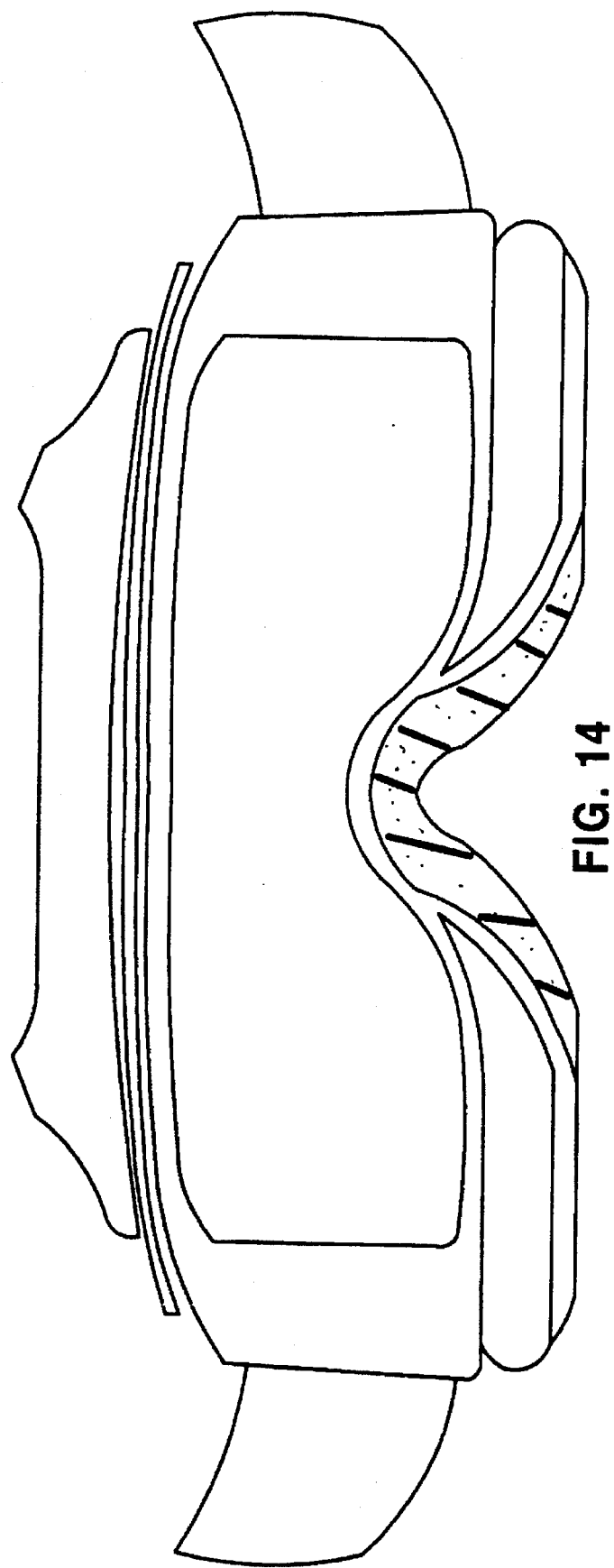
FIG. 14 shows the front view of a preferred embodiment of the present invention with a faring molded ventilation control valve.
Figure 15:
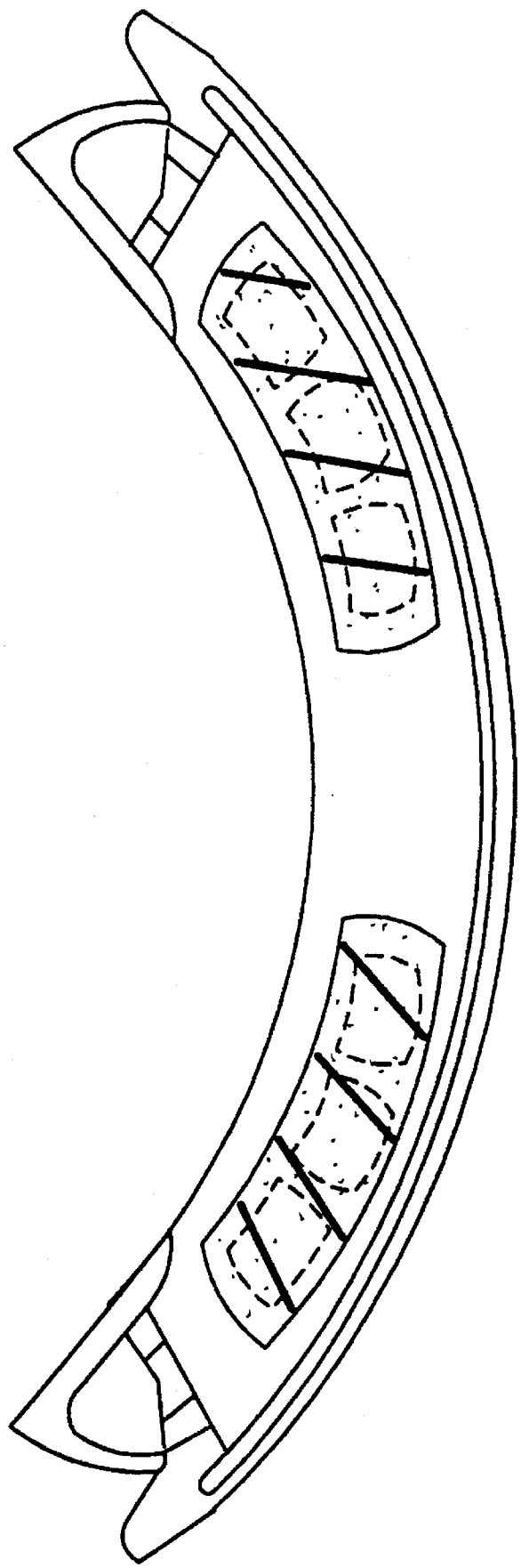
FIG. 15 shows a cross section of the inlet ports of the preferred embodiment shown in FIG. 14.

A third preferred embodiment is shown in FIG. 13. In this embodiment the valve plate and faring 55 are molded in one piece and move as a unit. The faring covers the valve and prevents snow and mud from covering the exhaust ports in the valve. Valve plate-faring 55 is held in place by screws 14 (not shown) which pass through the valve plate and top spacer and are screwed into and through BAR 16 (not shown).

Fourth Preferred Embodiment

Figure 16:
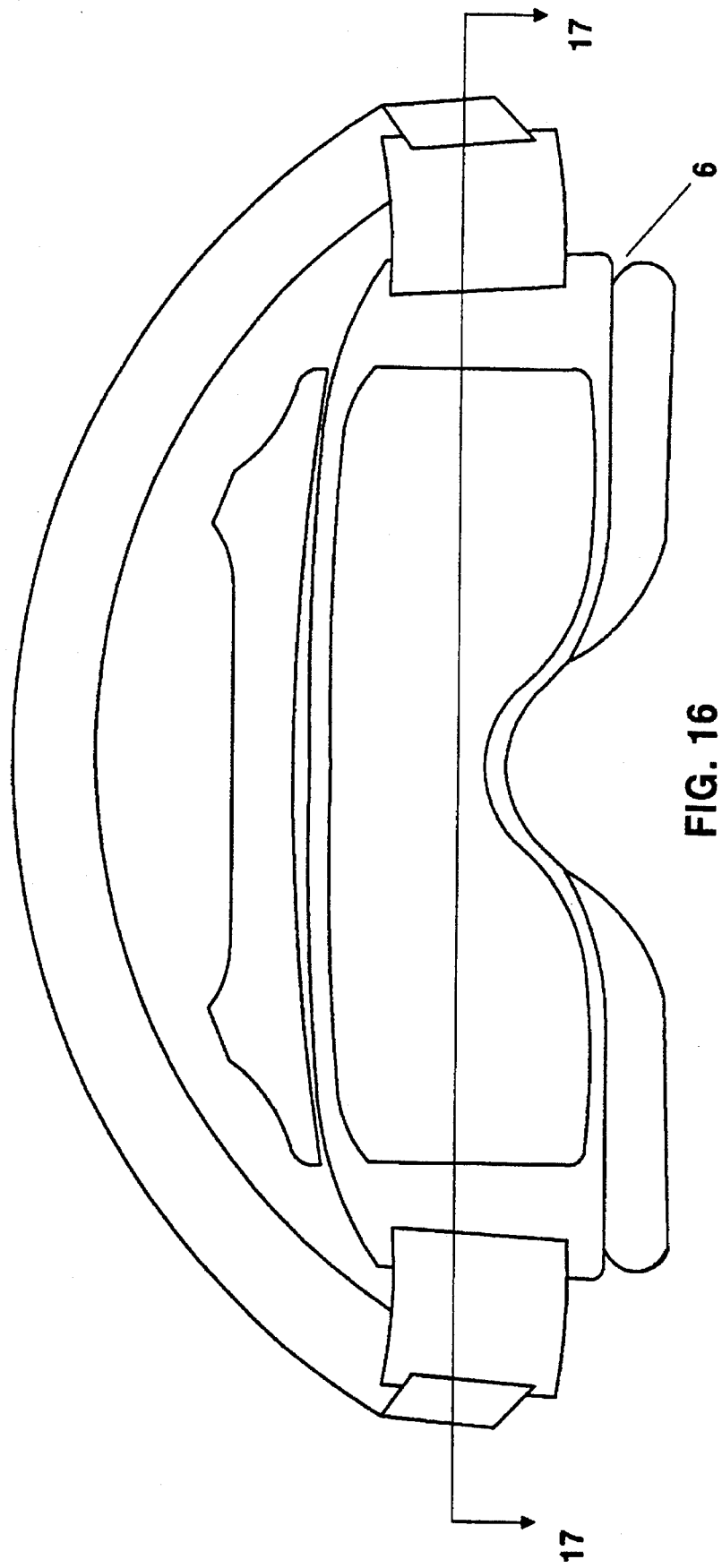
FIG. 16 shows a preferred embodiment for use with helmets.
Figure 17:
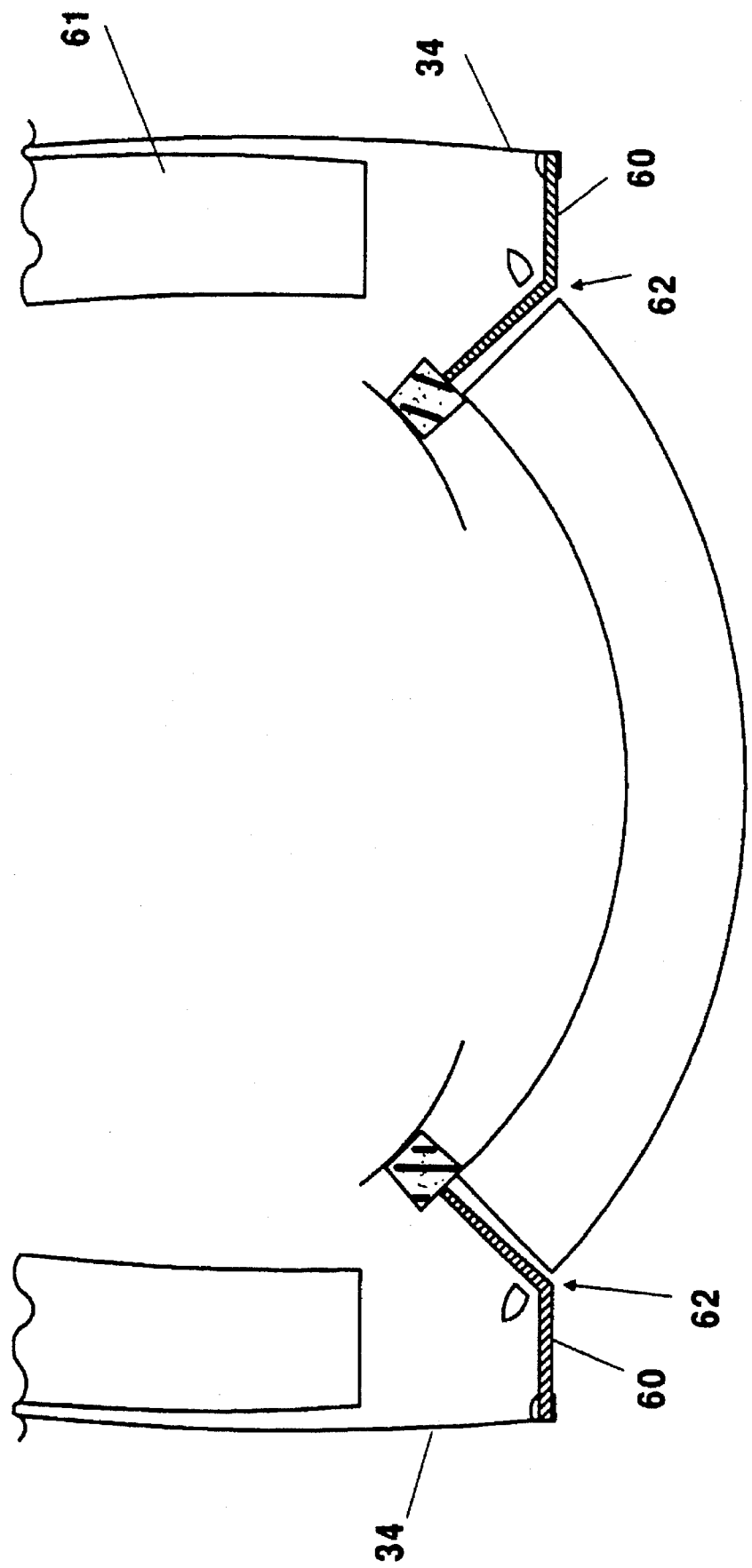
FIG. 17 shows a cross section of the cantilever of the preferred embodiment shown in FIG. 16.

A fourth preferred embodiment shown in FIGS. 16 and 17-17 is preferably worn over helmets such as motorcycle helmets. A cantilevered strap holder 60 attaches through strap slot 62 in the goggles frame 6. As strap 34 is pulled tight around the helmet, force is applied to the goggles frame maintaining pressure at interface between the goggles and the surface of the wearer's face.

Fifth Preferred Embodiment

In a fifth preferred embodiment, which is very useful for skiing in very heavy snow fall, I provide an opening about ½ square inch opening on the outboard sides of each air scoop at location 70 as shown in FIG. 1. These are snow escape ports which allow snow which would otherwise build up in the scoop to blow out through the openings. The cross section of the escape ports is small enough so that they do not significantly affect the flow through the goggles.

Alternate Method of Practicing Invention

An alternate method of practicing this invention is to provide kits to modify popular goggles already on the market to provide controlled air flow through them. The kits would preferably contain air scoops similar to air scoop 2 shown on the drawings. These could be modified so they would clip on the bottom of the goggles. These kits would also contain a slide valve plate similar to plate 12 shown in the figures. For some existing goggles a top spacer similar to spacer 8 would also be provided but with some other models, the kit user would be instructed to drill holes at specified locations in the top of the goggles.

Goggles Test

I have tested my goggles against several of the most popular "non-fogging" goggles. The following table lists the location, general weather conditions, comparison goggles and the results of my tests. The results follow:

| LOCATION AND DATE | WEATHER CONDITIONS | GOGGLES TYPE | RESULTS |
| --- | --- | --- | --- |
| Mt. Bachelor, Or 12-22-93–12-25-93 | Clear skies, No snow Temp. 20's 30% Rel Hum | Smith Scott Oakley Crooks | Experienced fogging of glasses after aggressive skiing and while waiting in line No fogging with vent valve wide open |
| Northstar Lake Tahoe CA 12-27-93–12-28-93 | Cloudy, light snow on & off Temp. 20's 70%/Rel Hum | Smith Scott Oakley Crooks | Experienced fogging of glasses after aggressive skiing and while waiting in line No fogging |
| Mammoth Mt, CA 1-7-94 to 1-9-94 | Clear and sunny Temp. 30–40's, 30% Rel Hum | Smith Scott Oakley Crooks | Experienced fogging of glasses after aggressive skiing and while waiting in line No fogging |
| Mammoth Mt, CA 2-11-94 | Snowing heavy at times Temp. 20's 100% Rel Hum | Uvex Oakley Crooks | Experienced fogging of glasses while skiing and while waiting in line No fogging |
| 2-12-94 to 2-13-94 | Clear sunny | Crooks | No Fogging |
| Mammoth Mt, CA 3-4-94 & 3-5-94 | Clear sunny temp 30 40's 30% Rel Hum | Crooks | No fogging |
| Mammoth Mt, CA 3-6-94 | Snowing Windy 20's 90% Rel Hum | Smith Scott Crooks | Fogging while skiing aggressively and waiting in lines No fogging |
| Banff, Canada Sunshine Mt 3-15-94 & 3-16-9 | Heavy Snows & windy Temp. 10 to 20's 100% Rel Hum | Smith Scott Oakley Crooks | Experienced fogging of glasses all types of terrain and while waiting in line No fogging |
| Lake Louise Canada 3-17-94 to 3-19-94 | Snow at high elev Temp. 20s to 40s windy | Smith Scott Oakley Crooks | Fogging of glasses under varying conditions No fogging |

| LOCATION AND DATE | WEATHER CONDITIONS | GOGGLES TYPE | RESULTS |
|---|---|---|---|
| Copper Mt, Colo 3-17-94 to 3-26-94 | Snowing to White out | Bolle' Crooks | Fogging while skiing and in lift lines No fogging |
| 3-21-94 to 3-26-94 | Light snow partly cloudy temp 30s 50%/rel hum | Bolle' Crooks | Fogging during aggressive skiing No fogging |
| Mammoth Mt, CA 4-8-94 to 4-10-94 | Heavy snow at times Temp. 20s 30s rel hum 70% to 100% | Smith Scott Oakley Crooks | Experienced fogging of glasses after aggressive skiing and while waiting in line No fogging, Fogging after fall with scoop clogged |

The above test results prove that my invention is far superior to the prior art goggles against which my invention was compared. The comparison goggles, to the best of my knowledge are representative of "non-fogging" goggles currently available on the commercial ski goggle market. These results show that my invention constitutes a substantial improvement in the state of the art of ski goggles.

While the above description contains many specificities, the reader should not construe these as limitations on the scope of the invention, but merely as exemplifications of preferred embodiments thereof. For example, for high production runs the air scope 2 would be molded as a part of the goggle rather than glued in place. The tabs obviously could be placed on top of valve plate rather than in front. Those skilled in the art will envision many other possible variations are within its scope. Accordingly the reader is requested to determine the scope of the invention by the appended claims and their legal equivalents and not by the above examples.

I claim:

1. Goggles comprising:

a frame defining a front side, a rear side, a bottom side and a top side, a transparent lens secured across the front side of said frame, a securing means for detachably securing said frame to a face of a user so that said rear side of said frame abuts against the face of the user and thus forming a chamber between said frame, lens and the face of the user, at least one air scoop means located at the bottom side of said goggles comprising an air passage with a cross sectional area of at least one square inch open in the front side of said frame for permitting air to enter said chamber and, when said user is facing into a head wind, for forcing air into said chamber so as to cause a positive air pressure in said chamber as compared to ambient air pressure, and a valve means located at the top side of said goggles for controlling the amount of air entering said goggle through said scoop means.

2. Goggles as in claim 1 wherein said frame comprises a plurality of ventilation ports located in the top side of said frame and said valve means comprises a slidable plate with a plurality of ventilation ports spatially matched to the ports in the top side of said frame.

3. Goggles as in claim 2 wherein said plurality of ports are at least four ports.

4. Goggles as in claim 3 wherein at least two of said ports are covered with a light foam screen.

5. Goggles as in claim 1 and further comprising a faring means for prevention of snow or other material from clogging said valve means.

6. Goggles as in claim 1 wherein said air scoop means define two outboard sides and said scoop means comprises a snow escape port located in each outboard side.

7. Goggles as in claim 1 wherein said securing means comprises a strap means for providing a pressure interface between the goggles frame and the face of the user.

8. Goggles as in claim 7 for use with helmets wherein said securing means further comprises a cantilevered strap holder means for increasing to the pressure interface between said goggles and the user's face.

9. Goggles as in claim 2 wherein at least one but not all of said plurality of ventilation ports is covered with a light foam screen.

* * * * *